United States Patent [19]

Manoury et al.

[11] Patent Number: 4,853,387
[45] Date of Patent: Aug. 1, 1989

[54] PIPERIDINE DERIVATIVES, AND THEIR APPLICATION IN THERAPY

[75] Inventors: Philippe Manoury, Verrières le Buisson; Jean Binet, Breuillet; Elisabeth Dewitte, Saint Gratien, all of France

[73] Assignee: Synthelabo, Paris, France

[21] Appl. No.: 223,076

[22] Filed: Jul. 22, 1988

[30] Foreign Application Priority Data

Jul. 23, 1987 [FR] France .................. 87 10408

[51] Int. Cl.[4] .................. A61K 31/495; C07D 239/02
[52] U.S. Cl. .................. 514/272; 514/275; 544/321; 544/330; 544/332
[58] Field of Search .................. 544/321, 332, 330; 514/272, 275

[56] References Cited

U.S. PATENT DOCUMENTS 4,617,393 10/1986 Bagli et al. .................. 544/321

OTHER PUBLICATIONS

Chemical Abstracts 160005y, vol. 77, 1972.

*Primary Examiner*—Mary C. Lee
*Assistant Examiner*—J. Richter

*Attorney, Agent, or Firm*—Fleit, Jacobson, Cohn, Price, Holman & Stern

[57] ABSTRACT

A compound which is a piperidine derivative of formula (I)

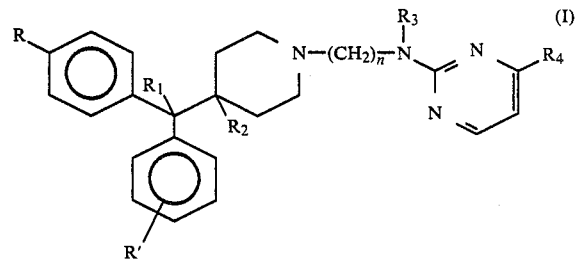

in which:
n is 1, 2, 3 or 4,
R is hydrogen or a halogen,
R', which is identical to R, is hydrogen or a halogen,
either $R_1$ is H or OH and $R_2$ is H, or $R_1$ and $R_2$ together denote a bond,
$R_3$ is hydrogen or ($C_{1-4}$) alkyl, and
$R_4$ is H or OH,
including tautomeric forms thereof, or a pharmaceutically acceptable acid addition salt thereof.

7 Claims, No Drawings

PIPERIDINE DERIVATIVES, AND THEIR APPLICATION IN THERAPY

The present invention relates to piperidine derivatives, their preparation and their application in therapy.

The present invention provides a compound of formula (I) as shown in Appendix 1, in which:

n is 1, 2, 3 or 4,
R is hydrogen or a halogen,
R' which is identical to R, is hydrogen or a halogen,
either $R_1$ is H or OH and $R_2$ is H, or $R_1$ and $R_2$ together denote a bond,
$R_3$ is hydrogen or $(C_{1-4})$alkyl, and
$R_4$ is H or OH,
including tautomeric forms thereof,
or a pharmaceutically acceptable acid addition salt thereof.

When $R_4$ is OH, the tautomeric forms of the compounds, as illustrated in Appendix 1, form part of the invention.

Preferred compounds are those in which n is 2, R and R' are fluorine, R' is in the 4-position and/or $R_3$ is methyl. Examples of compounds of formula (I) are shown in the following table ple chlorine or bromine, and n' and $R_5$ are as defined above.

The starting compounds of formula (II) are piperidines described in the literature, for example in U.S. Pat. No. 2,804,422 and Belgian Pat. No. 836,394.

The compounds of formula $X-(CH_2)_{n'}-R_5$ are described in J. D. Billimoria and K. O. Lewis, J. Chem. Soc, 1404, 1968.

A compound of formula (I) in which $R_1$ and $R_2$ together denote a bond may also be obtained from the corresponding compound of formula (I) in which $R_1$ is OH and $R_2$ is H, by dehydration in a strong acid medium.

The compounds of the invention may be useful for the treatment of migraine, anxiety, depression, obesity, inflammation, asthma, allergies, vascular or gastrointestinal spasms, hypertension and platelet aggregation, and as antiemetics.

Some compounds also possess antihistaminic activity. The daily dosage generally ranges from 5 to 200 mg The compounds of the invention may be administered orally or parenterally.

The present invention also provides a pharmaceutical composition comprising a compound of formula (I) and a pharmaceutically acceptable excipient.

| Compound | n | R | R' | $R_1$ | $R_2$ | $R_3$ | $R_4$ | m.p. (°C.) | salt |
|---|---|---|---|---|---|---|---|---|---|
| 1 | 2 | H | H | OH | H | H | H | 76 | — |
| 2 | 2 | H | H | OH | H | H | OH | 240-243 | fumarate |
| 3 | 2 | H | H | OH | H | $CH_3$ | OH | 163-165 | — |
| 4 | 2 | H | H | OH | H | $CH_3$ | H | 211-212 | HCl |
| 5 | 2 | H | H | bond | | $CH_3$ | OH | 177-180 | — |
| 6 | 2 | H | H | bond | | $CH_3$ | H | 98-100 | — |
| 7 | 2 | F | 4-F | OH | H | $CH_3$ | OH | 166-167 | — |
| 8 | 2 | F | 4-F | OH | H | $CH_3$ | H | 170-173 | — |
| 9 | 2 | F | 4-F | bond | | $CH_3$ | H | 187-189 | fumarate |
| 10 | 2 | F | 4-F | bond | | $CH_3$ | OH | 164-165 | — |
| 11 | 2 | F | 4-F | H | H | $CH_3$ | OH | 190-192 | oxalate |
| 12 | 2 | F | 4-F | H | H | $CH_3$ | H | 222-225 | HCl |
| 13 | 2 | F | 4-F | H | H | H | H | 161-163 | fumarate |
| 14 | 2 | F | 4-F | H | H | H | OH | 234-235 | HCl |
| 15 | 2 | F | 3-F | OH | H | $CH_3$ | OH | 123-125 | — |
| 16 | 2 | F | 3-F | bond | | $CH_3$ | OH | 114-116 | — |
| 17 | 3 | F | 4-F | OH | H | $CH_3$ | H | 206-207 | oxalate |
| 18 | 3 | F | 4-F | bond | | $CH_3$ | H | 171-172 | fumarate |
| 19 | 3 | F | 4-F | bond | | $CH_3$ | OH | 211-213 | fumarate |
| 20 | 3 | F | 4-F | OH | H | $CH_3$ | OH | 144-146 | — |
| 21 | 4 | F | 4-F | bond | | $CH_3$ | OH | 124-126 | — |

According to the invention, a compound of formula (I) may be prepared according to the reaction scheme shown in Appendix 2.

The compound of formula (I) may be prepared by reacting a compound of formula (IV) in which R, R', $R_1$, $R_2$ and $R_3$ are as defined above with either 2-chloropyrimidine or 2-methylthio-4-pyrimidinone in a protic or aprotic solvent.

A compound of formula (III) in which R, R', $R_1$ and $R_2$ are as defined above and $R_5$ is cyano and n' is 1, 2 or 3 or $R_5$ is phthalimido or $NR_3$Trit, in which $R_3$ is hydrogen or $(C_{1-4})$alkyl and Trit is triphenylmethyl, and n' is 2, 3 or 4, is hydrogenated in the presence of Raney nickel if $R_5$ is cyano, or hydrolysed in the presence of hydrazine if $R_5$ is phthalimido or in the presence of hydrochloric acid if $R_5$ is $NR_3$Trit, to obtain the compound of formula (IV).

The compound of formula (III) may be prepared by reacting a compound of formula (II) in which R, R', $R_1$ and $R_2$ are defined above with a compound of formula $X-(CH_2)_{n'}-R_5$ in which X is a labile group, for exam- The present invention further provides a compound of formula (I) for use in a method of treatment of the human or animal body by therapy, especially for use in a method of treatment of migraine, anxiety, depression, obesity, inflammation, asthma, an allergy, vascular or gastrointestinal spasms, hypertension or platelet aggregation or of a condition requiring an antiemetic or antihistaminic compound.

Finally the present invention provides the use of a compound of formula (I) in the manufacture of a medicament for the treatment of migraine, anxiety, depression, obesity, inflammation, asthma, an allergy, vascular or gastrointestinal spasms, hypertension or platelet aggregation or of a condition requiring an antiemetic or antihistaminic compound.

The Examples which follow further illustrate the invention.

The analyses and the IR and NMR spectra confirm the structure of the compounds.

EXAMPLE 1

α,α-Diphenyl-1-[2-(pyrimidinylamino)ethyl]-4-piperidinemethanol

1.1.
2-{2-[4-(Hydroxydiphenylmethyl)-1-piperidinyl]-ethyl}-1,3-(1H,2H)-isoindoledione A mixture of 15 g (0.056 mole) of α,α-diphenyl-4-piperidinemethanol, 14.5 g (0.056 mole) of 2-(2-bromoethyl)-1,3-(1H,2H)isoindoledione and 6.7 g (0.063 mole) of sodium carbonate in 150 ml of methyl isobutyl ketone is brought to refluxing temperature for 5 hours.

After evaporation of the solvent, the residue is taken up with water and chloroform. The organic phase is washed with water, dried, filtered and evaporated. An oil is obtained, which crystallizes after purification on a silica column. A product melting at 166°–169° C. is obtained.

1.2.
1-(2-Aminoethyl)-α,α-diphenyl-4-piperidinemethanol

A solution of 11.7 g (0.026 mole) of the above derivative in 200 ml of methanol containing 1.3 ml of hydrazine is stirred for 12 h at room temperature. The mixture is evaporated to dryness and the residue taken up with water and acidified with hydrochloric acid. The insoluble material is filtered off and the aqueous phase then extracted with methylene chloride.

The aqueous phase is alkalinized and extracted with methylene chloride. The organic phase is washed with water, dried, filtered and evaporated.

A white product melting at 164°–166° C. is obtained.

1.3.
α,α-Diphenyl-1-[2-(2-pyrimidinylamino)ethyl]-4-piperidinemethanol 2 g ($6.4 \times 10^{-3}$ mole) of 1-(2-aminoethyl)-α,α diphenyl-4-piperidinemethanol is brought to reflux for 20 h with 0.75 g ($6.5 \times 10^{-3}$ mole) of 2-chloropyrimidine and 0.56 g of sodium bicarbonate in 25 ml of ethanol.

The mixture is evaporated under vacuum and the residue taken up with methylene chloride and water. The organic phase is dried, filtered and evaporated.

After chromatographic purification of the residual oil, a solid product melting at 76° C. is obtained.

EXAMPLE 2

2-{[2-{4-[Bis(4-fluorophenyl)methyl]-1-piperidyl}ethyl]amino}-4(1H)-pyrimidinone

2.1.
2-{4-[Bis(4-fluorophenyl)methyl]-1-piperidyl}ethanenitrile

A mixture of 28.7 g (0.1 mole) of 4-[bis(4-fluorophenyl)methyl]piperidine, 11.7 g (0.11 mole) of sodium carbonate, 6.3 ml (0.1 mole) of 2-chloroethanenitrile and a few crystals of sodium iodide in 150 ml of methyl isobutyl ketone is heated to reflux for 4 h.

The reaction mixture is evaporated and the residue taken up with methylene chloride and water. The organic phase is dried, filtered and evaporated.

The residual oil crystallizes in isopropyl ether. (M.p. 114°–116° C.).

2.2.
2-{4-[Bis(4-fluorophenyl)methyl]-1-piperidyl}-ethanamine 11.0 g ($3.4 \times 10^{-2}$ mole) of the above product, dissolved in 150 ml of ethanol saturated with ammonia, is hydrogenated at 80° C. in the presence of Raney nickel under a hydrogen pressure of 60 bars.

When the absorption of hydrogen is complete, the catalyst is filtered off and the residue evaporated to dryness.

The residual oil is distilled. (B.p. 180° C. under 0.05 mm of mercury).

2.3.
2-{[2-{4-[Bis(4-fluorophenyl)methyl]-1-piperidyl}-ethyl]amino}-4(1H)-pyrimidinone 2 g ($1.4 \times 10^{-2}$ mole) of S-methylthiouracil and 4.6 g ($1.4 \times 10^{-2}$ mole) of 2-{4-[bis(4-fluorophenyl)-methyl]-1-piperidyl}ethanamine in 75 ml of toluene is heated under reflux for 48 h under an argon atmopshere.

The solvent is evaporated off and the residual oil purified by chromatography on a silica column.

The hydrochloride is prepared in isopropanol. (M.p. 234°–237° C.).

EXAMPLE 3

2-{[2-{4-[Bis(4-fluorophenyl)methylene]-1-piperidyl}ethyl]methylamino}-4(1H)-pyrimidinone

3.1.
4-[Bis(4-fluorophenyl)methylene]-N-methyl-1-piperidineethanamine 14.3 g (0.05 mole) of 4-[bis(4-fluorophenyl)-methylene]piperidine and 9.5 g (0.025 mole) of 2-bromo-N-methyl-N-(triphenylmethyl)ethanamine dissolved in 75 ml of toluene are heated to reflux.

When the reaction is complete, the mixture is cooled and the precipitate filtered off. The filtrate is evaporated and the residual oil taken up with 250 ml of N HCl. The mixture is heated to 50° C. for 1 h and left standing overnight, and the precipitate is filtered off. The filtrate is extracted with ether and the aqueous phase is then alkalinized with sodium hydroxide and extracted with methylene chloride. The organic phase is washed with water, dried, filtered and evaporated.

A product is obtained in the form of an oil, which is used in the crude state for the next stage of the synthesis.

3.2.
2-{[2-{4-[Bis(4-fluorophenyl)methylene]-1-piperidyl}ethyl]methylamino}-4(1H)-pyrimidinone 1 g ($2.9 \times 10^{-3}$ mole) of the above amine, dissolved in 50 ml of toluene, is heated to reflux under argon for 48 h with 0.5 g ($2.9 \times 10^{-3}$ mole) of S-(methyl)-thiouracil. The solution is evaporated to dryness and the residual oil purified by chromatography on a silica column. A product melting at 164°–165° C. is obtained.

EXAMPLE 4

1-{2-[Methyl-(2-pyrimidinyl)amino]ethyl}-α,α-di-phenyl-4-piperidinemethanol

4.1.
1-[2-(methylamino)ethyl]-α,α-diphenyl-4-piperidinemethanol

A mixture of 26.7 g (0.1 mole) of α,α-diphenyl-4-piperidinemethanol, 38 g (0.1 mole) of N-methyl-N-trityl-2-bromoethanamine and 8.4 g (0.1 mole) of sodium bicarbonate in 400 ml of methyl isobutyl ketone is heated to reflux for 48 h. The mixture is then filtered while boiling and the filtrate left to stand, the precipitate obtained is filtered off and dried.
M.p. 202°–205° C.

The precipitate is taken up with 300 ml of N HCl and stirred for 4 h at room temperature. The mixture is filtered and the precipitate washed with water.

The filtrate is alkalinized with concentrated sodium hydroxide and extracted with methylene chloride. The organic phase is washed with water, dried, filtered and evaporated. A product melting at 168°–170° C. is obtained.

4.2.
1-{2-[Methyl-(2-pyrimidinyl)amino]ethyl}-α,α-diphenyl-4-piperidinemethanol 4.9 g (0.015 mole) of 1-[2-(methylamino)ethyl-α,α-diphenyl-4-piperidinemethanol, 1.7 g (0.015 mole) of 2-chloropyrimidine and 1.3 g of sodium bicarbonate in 75 ml of ethanol are brought to reflux under an argon atmosphere. Refluxing is maintained for 24 h and the mixture is cooled and filtered. The filtrate is evaporated, the residue taken up with ether and the organic phase washed with water, dried, filtered and evaporated.

The hydrochloride is prepared in ethanol.
M.p. 211°–212° C.

EXAMPLE 5

4-(Diphenylmethylene)-N-methyl-N-(2-pyrimidinyl)-1-piperidineethanamine

The hydrochloride of Example 4 is taken up in 100 ml of 6N hydrochloric acid and the mixture is brought to reflux for 2 h. The solution is cooled and poured into ice. The mixture is alkalinized with sodium hydroxide and extracted with methylene chloride. The organic phase is washed with water, dried, filtered and evaporated. A product melting at 98°–100° C. is obtained.

EXAMPLE 6

2-{[2-{4-[Bis(4-fluorophenyl)hydroxymethyl]-1-piperidyl}ethyl]methylamino}-4(1H)-pyrimidinone

6.1.
α,α-Bis(4-fluorophenyl)-1-{2-[(methyl)(triphenylmethyl)amino]ethyl}-4-piperidinemethanol The product is prepared using the process described in 4.1., starting with 22.0 g (0.072 mole) of α,α-bis(4-fluorophenyl)-4-piperidinemethanol, 27.6 g (0.072 mole) of 2-bromo-N-methyl-N-(triphenylmethyl)-ethanamine, 6.7 g of sodium bicarbonate and 200 ml of methyl isobutyl ketone.
M.p. 100° C.

6.2.
α,α-Bis(4-fluorophenyl)-1-[2-(methylamino)ethyl]-4-piperidinemethanol

The hydrolysis is carried out as in 4.1., starting with 41 g (0.068 mole) of the above product.
M.p. 146°–148° C.

6.3.
2-{[2-{4-[Bis(4-fluorophenyl)hydroxymethyl]-1-piperidyl}ethyl]methylamino}-4(1H)-pyrimidinone The product is prepared as described in 3.2., starting with 7 g (0.02 mole) of the above product and 2.8 g (0.02 mole) of S-(methyl)thiouracil in 100 ml of toluene.
M.p. 166°–167° C.

The compounds of the invention possess an antiserotonin activity (in respect of the 5HT2 type receptors).

This activity was demonstrated "in vitro" by the displacement of ligands bound specifically to serotoninergic receptors (SBS binding test), and "in vivo" by antagonism of the effects of serotonin at the peripheral level (OES test) and at central level (AHT test).

SBS Test: the compounds of the invention were subjected to a test of displacement of the binding of spiroperidol to the serotoninergic (5-HT2) receptors of rat cerebral cortex.

For this test, rat brains are removed and the cortex is dissected out and homogenized at 0° C. in 10 volumes of a mixture containing, per liter, 50 millimoles of Tris/HCl buffer at pH 7.4, 120 millimoles of sodium chloride and 5 millimoles of potassium chloride. The homogeneous mixture is centrifuged at 40,000×g for 10 min, and the pellet is then recovered twice, washed by suspending it in the same buffer mixture, homogenized again and centrifuged. Lastly, the final pellet is diluted in the same buffer mixture in the proportion of 100 mg of wet tissue for 1 ml of buffer.

The tissue is then subjected to a prior 10-min incubation at 37° C. in the presence of 10 micromoles/l of pargyline, and then to a 20-min incubation at 37° C. in the presence of [$^3$H]spiroperidol (specific activity: 25.6 Ci per millimole) at a concentration of 0.3 nanomole/l and test compound at concentrations ranging from 0.0001 to 100 micromoles/l.

1-ml aliquots are removed and filtered under vacuum, and the filters are washed twice with 5 ml of cold buffer and dried. The radioactivity is measured in toluene in the presence of 5 g/l of 2,5-diphenyloxazole (PPO) and 0.1 g/l of 1,4-bis(5-phenyl-2-oxazolyl)benzene (POPOP).

To assess the activity of the compounds, the curve is plotted for the percentage inhibition of the specific binding of [$^3$H]spiroperidol as a function of the concentration of displacing drug. The IC$_{50}$ concentration, the concentration between 50% of the specific binding, is determined graphically.

The specific binding is defined as the binding displaced by 100 micromoles/l of 5-HT.

The IC$_{50}$ concentrations of the compounds of the invention lie for the most part between 1 and 50 nanomoles/l.

OES Test: the antiserotoninergic activity of the compounds of the invention was also demonstrated by their effect on serotonin-induced oedema in rats, according to the method described by Maling et al, J. Pharmacol. Exp. Therap., 191 (2), 300–310 (1974).

The animals are CD strain male rats (Ch. River, France) weighing 120 to 150 g, fasted for 18 h and distributed in randomized sets.

The compounds, dissolved or suspended in Tween 80 at a concentration of 1%, are administered orally in the proportion of 0.5 ml for 100 g of body-weight, 1 h before the sub-plantar injection of 1 μg of serotonin (dissolved in sterile physiological saline, in a volume of 0.1 ml) into one of the hind legs. The volume of oedema is measured 1 h after the injection of serotonin by means of an Ugo Basile mercury plethysometer. The $AD_{40}$ (dose which decreases by 40% the volume of the oedema, relative to the control animals) is determined graphically.

The $AD_{40}$ of the compounds of the invention, determined orally, is between 0.1 and 2 mg/kg.

AHT Test: the antiserotoninergic activity of the compounds was studied in respect of their effect on the antagonism of "head-twitches" induced by L-5-hydroxytryptophan (L-5-HTP) in mice, according to the method described by Corne et al, Br. J. Pharmacol., 20, 106–120 (1962).

The mice (CD1 males, Charles River France; 18–22 g of bodyweight) receive the test products at increasing doses, or the solvent, intraperitoneally or orally, simultaneously (i.p. administration) or 60 minutes before (oral administration) a subcutaneous injection of L-5-HTP at a dose of 250 mg/kg. Forty-five minutes after this injection of 5-HTP, the number of twitches is counted, for each mouse, for 1 minute.

For each treatment, the mean number of twitches, as well as the percentage variation relative to the control batch, are calculated.

From the dose-response curve, the $AD_{50}$ (50% active dose or dose which decreases by 50% the mean number of twitches relative to the control animals) is determined by the graphic method of Miller and Tainter (Proc. Soc. Exp. Biol. Med., (1944), 57, 261).

The $AD_{50}$ values of the compounds of the invention are generally from 0.05 to 2 mg/kg intraperitoneally and 0.1 to 4 mg/kg orally.

Appendix 1

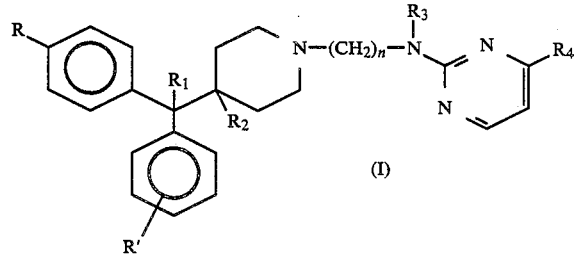

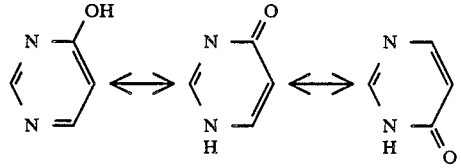

Appendix 2

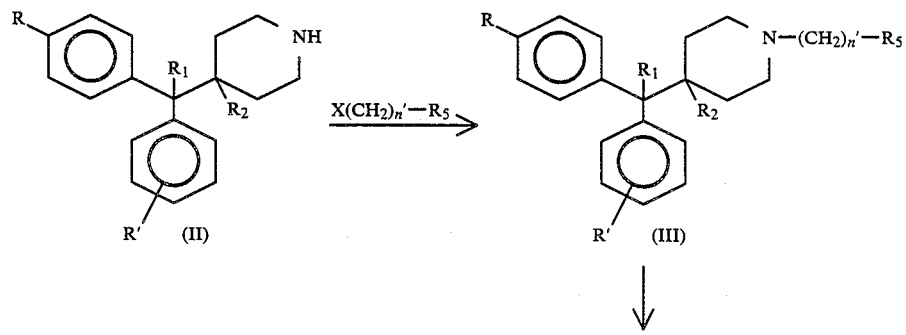

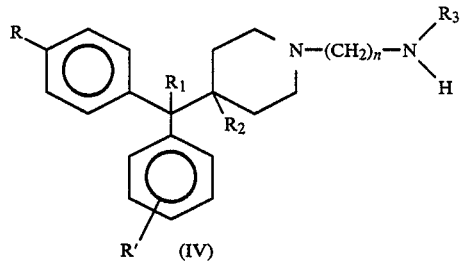

(IV)

↙ 2-chloropyrimidine
or
2-methylthio-4-pyrimidinone

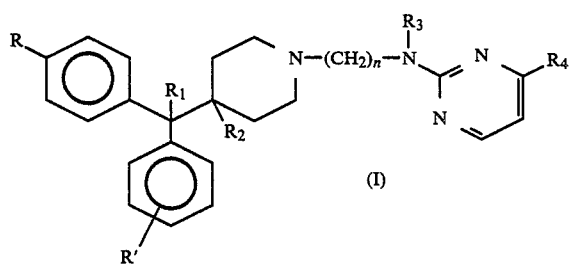

(I)

We claim:
1. A compound which is a piperidine derivative of formula (I)

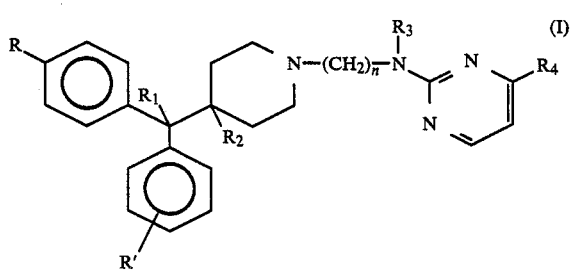

in which:
n is 1, 2, 3 or 4,
R is hydrogen or a halogen,
R', which is identical to R, is hydrogen or a halogen,
either $R_1$ is H or OH and $R_2$ is H, or $R_1$ and $R_2$ together denote a bond,
$R_3$ is hydrogen or $(C_{1-4})$alkyl, and
$R_4$ is H or OH,
including tautomeric forms thereof, or a pharmaceutically acceptable acid addition salt thereof.

2. A compound according to claim 1 in which n is 2.

3. A compound according to claim 1 in which R and R' are fluorine.

4. A compound according to claim 1 in which R' is in the 4-position.

5. A compound according to claim 1 in which $R_3$ is methyl.

6. A pharmaceutical composition comprising a pharmaceutically effective amount of a compound of formula (I) as defined in claim 1 and a pharmaceutically acceptable excipient.

7. A method of treatment of migraine, anxiety, depression, obesity, inflammation, asthma, an allergy, vascular or gastrointestinal spasms, hypertension or platelet aggregation or of a condition requiring an antiemetic or antihistaminic compound, which comprises administering to a subject suffering or liable to suffer therefrom an effective amount of a compound of formula (I) as defined in claim 1.

* * * * *